(12) United States Patent
Yamada et al.

(10) Patent No.: US 9,909,158 B2
(45) Date of Patent: Mar. 6, 2018

(54) METHOD OF PRODUCING SUGAR SOLUTION INCLUDING WASHING WITH AQUEOUS ALKALINE AND INORGANIC SALT SOLUTIONS

(71) Applicant: Toray Industries, Inc., Tokyo (JP)

(72) Inventors: Chiaki Yamada, Kamakura (JP);
Hiroyuki Kurihara, Kamakura (JP);
Katsushige Yamada, Kamakura (JP)

(73) Assignee: Toray Industries, Inc. (JP)

( * ) Notice: Subject to any disclaimer, the term of this patent is extended or adjusted under 35 U.S.C. 154(b) by 0 days.

(21) Appl. No.: 14/412,217

(22) PCT Filed: Jul. 1, 2013

(86) PCT No.: PCT/JP2013/067977
§ 371 (c)(1),
(2) Date: Dec. 31, 2014

(87) PCT Pub. No.: WO2014/007189
PCT Pub. Date: Jan. 9, 2014

(65) Prior Publication Data
US 2015/0167037 A1    Jun. 18, 2015

(30) Foreign Application Priority Data
Jul. 3, 2012 (JP) .................. 2012-149382

(51) Int. Cl.
| | | |
|---|---|---|
| C12N 9/42 | (2006.01) | |
| A61K 38/47 | (2006.01) | |
| C12P 19/14 | (2006.01) | |
| C12P 19/02 | (2006.01) | |
| C13K 1/04 | (2006.01) | |
| C13K 1/02 | (2006.01) | |

(52) U.S. Cl.
CPC ............ *C12P 19/14* (2013.01); *C12N 9/2434* (2013.01); *C12N 9/2437* (2013.01); *C12P 19/02* (2013.01); *C13K 1/02* (2013.01); *C13K 1/04* (2013.01)

(58) Field of Classification Search
CPC .. C12P 19/14; C13K 1/02; C13K 1/04; C12N 9/2434; C12N 9/2437; C12N 9/42; A61K 78/47
USPC ...................... 424/94.61; 435/209
See application file for complete search history.

(56) References Cited

U.S. PATENT DOCUMENTS

2011/0250637 A1* 10/2011 Kurihara .............. B01D 61/022
435/41
2013/0059345 A1    3/2013 Kurihara et al.

FOREIGN PATENT DOCUMENTS

| JP | 2012-223113 A | 11/2012 |
|---|---|---|
| WO | 2010/067785 A1 | 6/2010 |
| WO | 2011/115039 A1 | 9/2011 |
| WO | 2013/039137 A1 | 3/2013 |

OTHER PUBLICATIONS

Reese, E.T. Elution of Cellulase From Cellulose; Process Biochemistry, vol. 17, No. 3 (1982) pp. 1-28.*
Zhu et al. Direct Quantitative Determination of Adsorbed Cellulase on Lignocellulosic Biomass With its Application to Study Cellulase Desorption for Potential Recycling; Analyst, vol. 134 (2009) pp. 2267-2272.*
Zhiguang Zhu et al., "Direct quantitative determination of adsorbed cellulase on lignocellulosic biomass with its application to study cellulase desorption for potential recycling," Analyst, Nov. 2009, vol. 134, No. 11, pp. 2267-2272.
M.V. Deshpande et al., "Reutilization of enzymes for saccharification of lignocellulosic materials," Enzyme Microb. Technol., Aug. 1984, vol. 6, No. 8, pp. 338-340.
A.P. Sinitsyn et al., "Recovery of Enzymes from the Insoluble Residue fo Hydrolyzed Wood," Applied Biochemistry and Biotechnology, Feb. 1983, vol. 2, No. 1, pp. 25-29.
Jian Xu et al., "A Novel Stepwise Recovery Strategy of Cellulase Adsorbed to the Residual Substrate after Hydrolysis of Steam Exploded Wheat Straw," Appl. Biochem. Biotechnol., Oct. 2007, vol. 143, No. 1, pp. 93-100.
D.E. Otter et al., "Desorption of *Trichoderma reesei* Cellulase from Cellulose by a Range of Desorbents," Biotechnology and Bioengineering, Jul. 1989, vol. 34, No. 3, pp. 291-298.
D.E. Otter et al., "Elution of *Trichoderma Reesei* from Cellulose by pH Adjustment with Sodium Hydroxide," Biotechnology Letters, Jun. 1984, vol. 6, No. 6, pp. 369-374.

\* cited by examiner

*Primary Examiner* — Scott Long
*Assistant Examiner* — Paul Martin
(74) *Attorney, Agent, or Firm* — DLA Piper LLP (US)

(57) ABSTRACT

A method of producing a sugar liquid from a cellulose-containing biomass includes (1) hydrolyzing a cellulose-containing biomass using a filamentous fungus-derived cellulose and carrying out solid-liquid separation into a sugar liquid and a hydrolysis residue; (2) washing the hydrolysis residue in (1) using an aqueous alkaline solution and an aqueous inorganic salt solution independently and recovering, as a washing liquid, the filamentous fungus-derived cellulase adsorbed to the hydrolysis residue; and (3) filtering the washing liquid in (2) through an ultrafiltration membrane to recover a sugar liquid as a permeate and the filamentous fungus-derived cellulase as a non-permeate.

8 Claims, 2 Drawing Sheets

METHOD OF PRODUCING SUGAR SOLUTION INCLUDING WASHING WITH AQUEOUS ALKALINE AND INORGANIC SALT SOLUTIONS

TECHNICAL FIELD

This disclosure relates to a method of producing a sugar liquid from a cellulose-containing biomass.

BACKGROUND

In recent years, methods of hydrolysis of a cellulose-containing biomass using enzymes, which methods use less energy and cause less environmental load but produce sugar at high yields have been extensively studied. However, methods using enzymes have a drawback in that the cost of the enzymes is high.

As methods of solving such a technical problem, methods in which an enzyme used for the hydrolysis is recovered and reused have been proposed. Among these methods, methods in which the enzyme adsorbed to the hydrolysis residue is recovered by washing with an aqueous alkaline solution are less costly and suitable for the purpose of reducing the cost of the enzyme. Thus, many studies have been carried out on such methods.

More specifically, a method in which the hydrolysis residue after enzymatic saccharification is washed with an aqueous sodium hydroxide solution at a pH of about 8 to recover the enzyme component from crystalline cellulose (D. E. Otter et al., "Elution of *Trichoderma reesei* Cellulose from Cellulose by pH Adjustment with Sodium Hydroxide," Biotechnology Letters (1984), Vol. 6, No. 6, 369-374), and a method in which the enzyme adsorbed to crystalline cellulose or dilute sulfuric acid treated corn stover is recovered by washing with an aqueous alkaline solution at a pH of 10 to 13 (Z. Zhu et al., "Direct quantitative determination of adsorbed cellulose on lignocellulosic biomass with its application to study cellulose desorption for potential recycling," Analyst (2009), Vol. 134, 2267-2272) are known.

As a result of studying conventional methods of recovering the enzyme, we discovered that the type of the recovered enzyme is biased, and that reusability of the recovered enzyme is not sufficient. In view of this, we found that it could be helpful to increase reusability of filamentous fungus-derived cellulase recovered from a hydrolysis residue of a cellulose-containing biomass obtained using the filamentous fungus-derived cellulase, to thereby reduce the amount of the filamentous fungus-derived cellulase used in the method of producing a sugar liquid.

SUMMARY

We further discovered that, when a hydrolysis residue of a cellulose-containing biomass obtained using a filamentous fungus-derived cellulase is washed using an aqueous alkaline solution and an aqueous inorganic salt solution independently, enzyme components can be evenly eluted.

We thus provide [1] to [10]:

[1] A method of producing a sugar liquid from a cellulose-containing biomass, comprising:
Step (1): hydrolyzing a cellulose-containing biomass using a filamentous fungus-derived cellulase, and carrying out solid-liquid separation into a sugar liquid and a hydrolysis residue;
Step (2): washing the hydrolysis residue in Step (1) using an aqueous alkaline solution and an aqueous inorganic salt solution independently, and recovering, as a washing liquid, the filamentous fungus-derived cellulase adsorbed to the hydrolysis residue; and
Step (3): filtering the washing liquid in Step (2) through an ultrafiltration membrane to recover a sugar liquid as a permeate, and the filamentous fungus-derived cellulase as a non-permeate.

[2] The method of producing a sugar liquid according to [1], wherein, in Step (2), the hydrolysis residue is washed with the aqueous alkaline solution to recover an aqueous alkaline solution washing liquid as a first washing liquid, and further washed with the aqueous inorganic salt solution to recover an aqueous inorganic salt solution washing liquid as a second washing liquid.

[3] The method of producing a sugar liquid according to [1] or [2], wherein the pH of the aqueous alkaline solution in Step (2) is within the range of 7.5 to 10.0.

[4] The method of producing a sugar liquid according to any one of [1] to [3], wherein the temperature of the aqueous alkaline solution in Step (2) is not more than 40° C.

[5] The method of producing a sugar liquid according to any one of [1] to [4], wherein the alkali in Step (2) is ammonia, sodium hydroxide, potassium hydroxide, sodium carbonate, and/or trisodium phosphate.

[6] The method of producing a sugar liquid according to any one of [1] to [5], wherein the inorganic salt in Step (2) is one or more selected from the group consisting of sodium chloride, potassium chloride, magnesium chloride, and ammonium sulfate.

[7] The method of producing a sugar liquid according to any one of [1] to [6], wherein the filamentous fungus-derived cellulase in Step (1) is derived from a microorganism(s) belonging to the genus *Trichoderma*.

[8] The method of producing a sugar liquid according to any one of [1] to [7], wherein, in Step (1), a cellulose-containing biomass treated with dilute sulfuric acid is hydrolyzed.

[9] The method of producing a sugar liquid according to any one of [1] to [8], wherein the hydrolysis residue is obtained by press filtration in Step (1).

[10] The method of producing a sugar liquid according to any one of [1] to [9], comprising the step of filtering the sugar liquid obtained in Step (3) through a nanofiltration membrane and/or reverse osmosis membrane to recover a concentrated sugar liquid as a non-permeate.

Our methods allow even and highly efficient recovery of enzyme components, especially enzyme components involved in the cellobiose-degrading activity and the xylan-degrading activity, of a filamentous fungus-derived cellulase adsorbed to a hydrolysis residue of a cellulose-containing biomass so that the recovered filamentous fungus-derived cellulase can be used repeatedly.

DESCRIPTION OF SYMBOLS

Figure 1:
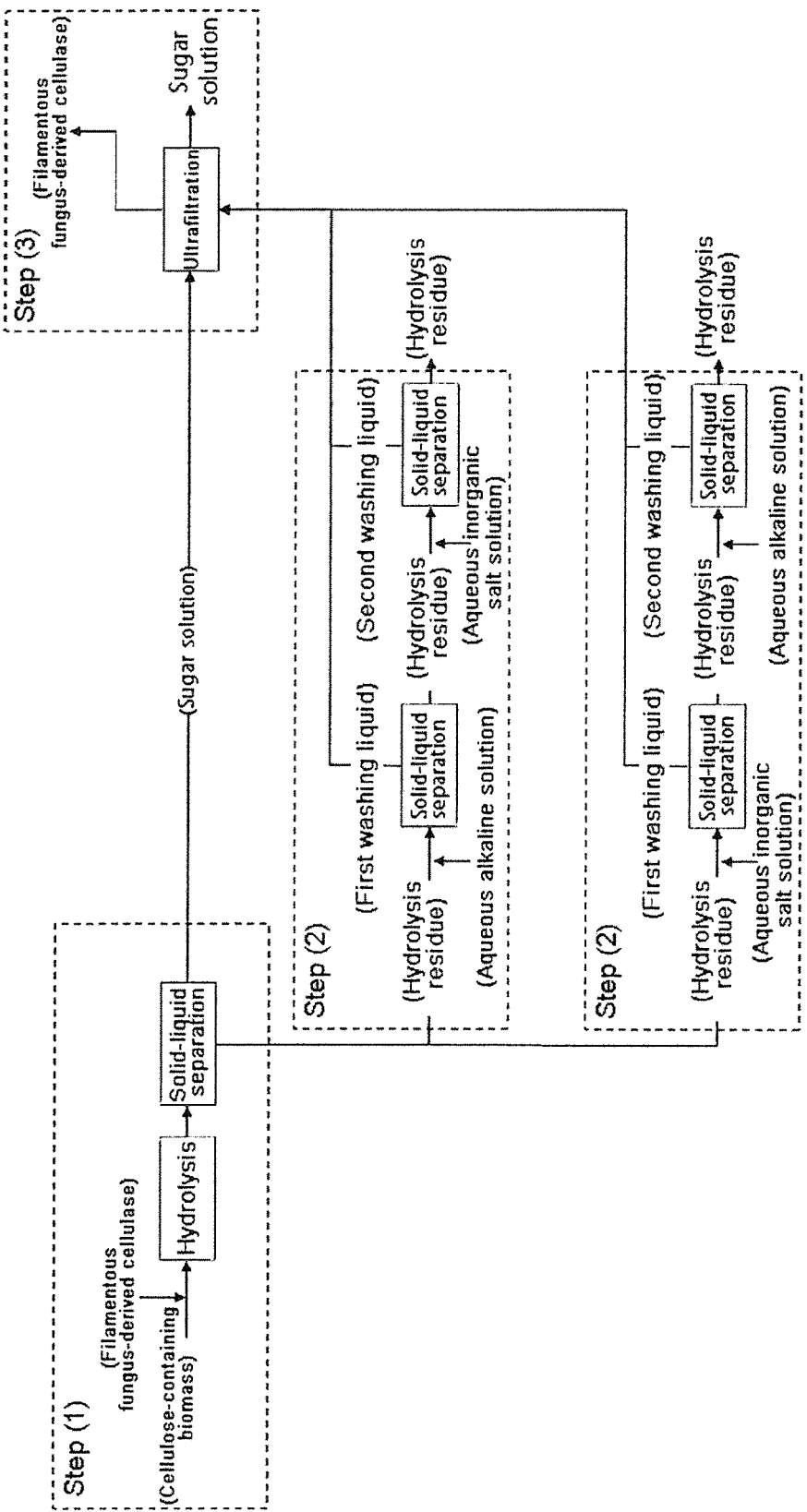
FIG. 1 is a schematic diagram showing an example of our method of producing a sugar liquid.

1 Incubator (hydrolysis tank)
2 Hydrolysis tank

3 Cellulose-containing biomass inlet
4 Stirrer (hydrolysis tank)
5 Water supply line (aqueous alkaline solution supply tank)
6 Aqueous alkaline solution supply tank
7 Incubator (aqueous alkaline solution supply tank)
8 Press filtration device
9 Compressor
10 Circulation line
11 Filtrate recovery tank
12 Ultrafiltration membrane device
13 Cellulase collection line
14 Hydrolysate inlet
15 Washing liquid port
16 pH sensor
17 Concentrated alkali supply tank
18 Stirrer 2 (concentrated alkali supply tank)
19 Water supply line 2 (aqueous inorganic salt solution supply tank)
20 Aqueous inorganic salt solution supply tank
21 Incubator 3 (aqueous inorganic salt solution supply tank)
22 Stirrer 3 (aqueous inorganic salt solution supply tank)

DETAILED DESCRIPTION

An example of carrying out our method is described below in the order corresponding to the Steps.
Step (1)

Examples of the cellulose-containing biomass include herbaceous biomasses such as bagasse, switchgrass, napier grass, *Erianthus*, corn stover, beet pulp, cottonseed hull, palm empty fruit bunch, rice straw, wheat straw, bamboo, and bamboo grass; and woody biomasses such as trees including *Betula alba* and *Fagus crenata*, and waste building materials. Since cellulose-containing biomasses contain not only cellulose and hemicellulose, which are constituted by sugars, but also lignin, which is an aromatic macromolecule; and the like, the efficiency of the enzymatic hydrolysis can be enhanced by performing a pretreatment. Examples of the method of the pretreatment of the cellulose-containing biomass include acid treatment, sulfuric acid treatment, dilute sulfuric acid treatment, acetic acid treatment, alkaline treatment, caustic soda treatment, ammonia treatment, hydrothermal treatment, subcritical water treatment, pulverization treatment, and steaming treatment. In view of efficiently recovering a wide range of enzyme components in the Step (2) described below, dilute sulfuric acid treatment is preferred.

A filamentous fungus-derived cellulase is used for hydrolysis of a cellulose-containing biomass. Examples of the filamentous fungus include microorganisms such as *Trichoderma, Aspergillus, Cellulomonas, Clostridium, Streptomyces, Humicola, Acremonium, Irpex, Mucor* and *Talaromyces*. The cellulase may also be derived from a mutant strain of such a microorganism prepared by mutagenesis using a mutagen, UV irradiation, or the like to enhance the cellulase productivity.

Filamentous fungus-derived cellulase is an enzyme composition comprising a plurality of enzyme components such as cellobiohydrolase, endoglucanase, exoglucanase, β-glucosidase, xylanase, β-xylosidase, and xyloglucanase, and has an activity to saccharify cellulose and/or hemicellulose by hydrolysis. Since such a plurality of enzyme components are contained in filamentous fungus-derived cellulase, efficient hydrolysis of cellulose and/or hemicellulose can be carried out by their synergistic effect or complementary effect. Thus, filamentous fungus-derived cellulase is preferably used.

Cellulase is a general term for the group of enzymes that hydrolyze cellulose. Specific examples of cellulase include cellobiohydrolase, endoglucanase, exoglucanase, and β-glucosidase.

Cellobiohydrolase is a general term for enzymes that begin continuous hydrolysis from the reducing end or non-reducing end of cellulose, to release cellobiose. The group of enzymes belonging to cellobiohydrolase are described as EC number: EC 3.2.1.91.

Endoglucanase is a general term for enzymes that hydrolyze cellulose molecular chains from their central portions. The group of enzymes belonging to endoglucanase are described as EC number: EC 3.2.1.4.

Exoglucanase is a general term for enzymes that hydrolyze cellulose molecular chains from their termini. The group of enzymes belonging to exoglucanase are described as EC number: EC 3.2.1.74.

β-glucosidase is a general term for enzymes that act on cellooligosaccharides or cellobiose. The group of enzymes belonging to β-glucosidase are described as EC number: EC 3.2.1.21.

Xylanase is a general term for enzymes that act on hemicellulose or especially xylan. The group of enzymes belonging to xylanase are described as EC number: EC 3.2.1.8.

β-xylosidase is a general term for enzymes that act on xylooligosaccharides. The group of enzymes belonging to xylosidase are described as EC number: EC 3.2.1.37.

Xyloglucanase is a general term for enzymes that act on hemicellulose or especially xyloglucan. The group of enzymes belonging to xyloglucanase are described as EC numbers: EC 3.2.1.4 and EC 3.2.1.151.

Such cellulase components can be separated by a known method such as gel filtration, ion exchange or two-dimensional electrophoresis, and the separated components can be subjected to determination of their amino acid sequences (by N-terminal analysis, C-terminal analysis or mass spectrometry) and identification by comparison with databases.

The enzyme activity of a filamentous fungus-derived cellulase can be evaluated based on its hydrolytic activities on polysaccharides such as the crystalline cellulose-degrading activity, carboxy-methyl cellulose (CMC)-degrading activity, cellobiose-degrading activity, xylan-degrading activity, and mannan-degrading activity. The main enzymes showing the crystalline cellulose-degrading activity are cellobiohydrolase and exoglucanase, which degrade cellulose from its terminal portions. The main enzyme showing the cellobiose-degrading activity is β-glucosidase. The main enzymes involved in the CMC-degrading activity are cellobiohydrolase, exoglucanase, and endoglucanase. The main enzymes showing the xylan-degrading activity are xylanase and β-xylosidase. The term "main" herein is used to mean that the component(s) is/are involved in the degradation to the highest extent(s), while other enzyme components are also involved in the degradation.

Since filamentous fungi produce cellulase in the culture liquid, the culture liquid may be used as it is as a crude enzyme agent, or enzymes may be purified and formulated by a known method to provide a filamentous fungus-derived cellulase mixture. When filamentous fungus-derived cellulase is purified and formulated, the cellulase formulation may also contain substances other than enzymes such as a protease inhibitor, dispersant, solubilizer, and/or stabilizer. Among these, the crude enzyme product is preferably used. The crude enzyme product is derived from a culture supernatant obtained after culturing a *Trichoderma* microorganism for an arbitrary period in a medium prepared such that the microorganism produces cellulase. The medium components to be used therefor are not limited, and a medium supplemented with cellulose to promote production of cellulase may be generally used. As the crude enzyme product, the culture liquid may be used as it is, or a culture supernatant processed only by removal of the *Trichoderma* fungus may be preferably used.

The weight ratios of enzyme components in the crude enzyme product are not limited and, for example, a culture liquid derived from *Trichoderma reesei* contains 50 to 95% by weight cellobiohydrolase, and also contains as other components endoglucanase, β-glucosidase, and the like. Microorganisms belonging to *Trichoderma* produce strong cellulase components into the culture liquid, while the β-glucosidase activity in the culture liquid is low since β-glucosidase is retained in the cells or on the cell surfaces. Therefore, β-glucosidase from a different species or from the same species may be added to the crude enzyme product. As the β-glucosidase from a different species, β-glucosidase derived from *Aspergillus* may be preferably used. Examples of the β-glucosidase derived from *Aspergillus* include Novozyme 188, which is commercially available from Novozyme. A gene may be introduced into a *Trichoderma* microorganism, and the *Trichoderma* microorganism that has undergone genetic recombination such that β-glucosidase is produced into the culture liquid may be cultured to provide a culture liquid having enhanced β-glucosidase activity.

Among filamentous fungi, *Trichoderma* fungi can be preferably used since *Trichoderma* fungi produce large amounts of enzyme components having high specific activities in hydrolysis of cellulose. Specific examples of the *Trichoderma*-derived cellulase include cellulases derived from *Trichoderma reesei* QM9414, *Trichoderma reesei* QM9123, *Trichoderma reesei* RutC-30, *Trichoderma reesei* PC3-7, *Trichoderma reesei* CL-847, *Trichoderma reesei* MCG77, *Trichoderma reesei* MCG80, and *Trichoderma viride* QM9123. Among these, cellulase derived from *Trichoderma reesei* is more preferred.

A filamentous fungus-derived cellulase is added to the cellulose-containing biomass to perform hydrolysis. The temperature during the hydrolysis reaction is preferably 40 to 60° C. and, especially when a *Trichoderma*-derived cellulase is used, the temperature is more preferably 45 to 55° C. The time of the hydrolysis reaction is preferably 2 hours to 200 hours. When the reaction time is less than 2 hours, sugar yield is insufficient, which is not preferred. On the other hand, when the reaction time is more than 200 hours, the enzyme activity decreases, which is not preferred since it adversely affects reusability of the recovered enzyme. The pH during the hydrolysis reaction is preferably 4.0 to 6.0. When a *Trichoderma*-derived cellulase is used as the filamentous fungus-derived cellulase, the optimum reaction pH is 5.0. Since the pH changes during the hydrolysis, it is preferred to perform the hydrolysis while maintaining a constant pH by addition of a buffer to the reaction liquid or use of an acid or alkali.

The hydrolysate obtained by the hydrolysis can be separated into a sugar liquid and a hydrolysis residue by solid-liquid separation. Examples of the method of solid-liquid separation include centrifugation and press filtration and recovering the solid by press filtration is preferred.

A reason why press filtration is preferred for the solid-liquid separation is as follows: 1) the recovery of the sugar solution is excellent; and 2) a clear filtrate can be obtained. The recovery of the sugar remaining in the solid side during the solid-liquid separation can be increased by increasing the amount of water added for washing of the residue. However, an increase in the water added results in a low sugar concentration in the sugar solution, which is not preferred. Therefore, in view of reducing the amount of the water as much as possible while achieving a high sugar recovery, the apparatus to carry out the solid-liquid separation is preferably a press filtration apparatus, with which a larger amount of sugar solution can be recovered by one time of solid-liquid separation. The sugar solution and the washing liquid of the residue, obtained by the solid-liquid separation, are filtered through an ultrafiltration membrane to recover enzyme components. The amounts of solids and particulate components contained in the liquid to be passed through the ultrafiltration membrane are preferably small in view of preventing membrane fouling. In press filtration, the amounts of solids and particulate components are small so that press filtration can preferably be used.

The sugar liquid obtained in Step (1) may be further subjected to concentration treatment to increase the sugar concentration. Examples of the concentration treatment include concentration by evaporation, concentration under reduced pressure, and membrane concentration. The method described in WO 2010/067785, which uses less energy and enables separation of fermentation inhibitors contained in the sugar liquid, can be used to obtain a concentrated sugar liquid in which sugar components are concentrated.

Step (2)

The hydrolysis residue obtained in the Step (1) is in a state where a relatively large amount of filamentous fungus-derived cellulase is adsorbed thereto. By washing the hydrolysis residue using an aqueous alkaline solution and an aqueous inorganic salt solution independently in Step (2), the adsorbed cellulase component is dissolved into the washing liquid, and recovered.

The aqueous alkaline solution is not limited as long as its pH is higher than 7, and an aqueous alkaline solution having a pH of 7.5 to 10.0 may be preferably used. When the pH is higher than 10.0, deactivation of cellulase may occur during the washing, while when the pH is lower than 7.5, the enzyme recovery may be insufficient.

The aqueous alkaline solution can be prepared by dissolving an alkali in water. The alkali is not limited as long as it is a substance having a pH higher than 7 when the substance is dissolved in water, and examples of the alkali include one or more selected from hydroxides of alkali metals and alkaline earth metals; ammonia; amines; carbonates of alkali metals; and phosphates of alkali metals. In particular, in view of solubility in water and the capacity to adjust the pH to a desired value even by use of a small amount of the alkali, more preferred examples of the alkali include ammonia, sodium hydroxide, potassium hydroxide, sodium carbonate and trisodium phosphate. In view of obtaining the maximum effect, still more preferred examples of the alkali include ammonia.

During the washing of the hydrolysis residue using the aqueous alkaline solution, the pH may decrease due to components extracted from the hydrolysis residue. Therefore, it is desired to keep a constant pH by addition of an alkali as appropriate. The alkali to be added may be either a liquid or solid, and, in view of quickly adjusting the pH, a liquid is preferably used.

The washing of the hydrolysis residue using the aqueous alkaline solution is preferably carried out at a temperature of not more than 40° C. Cellulase is unstable under alkaline conditions, and washing at a temperature higher than 40° C. may cause deactivation of the enzyme, resulting in low reusability of the enzyme.

The washing time of the hydrolysis residue using the aqueous alkaline solution is not limited, and preferably 5 to 180 minutes. When the washing time is less than 5 minutes, elution of the cellulase adsorbed to the hydrolysis residue may be insufficient, while when the washing time is more than 180 minutes, cellulase may be deactivated.

The aqueous inorganic salt solution is not limited, and examples of the aqueous inorganic salt solution include aqueous solutions of one or more selected from sodium salt, potassium salt, magnesium salt, sulfuric acid salt, ammonium salt, hydrochloric acid salt, phosphoric acid salt, and nitric acid salt. More preferred examples of the inorganic salt include sodium chloride, sodium sulfate, sodium hydrogen sulfate, sodium dihydrogen phosphate, disodium hydrogen phosphate, ammonium sulfate, potassium chloride, ammonium chloride, magnesium chloride, and magnesium sulfate, which have high solubility in water. The inorganic salt is most preferably sodium chloride, potassium chloride, magnesium chloride, or ammonium sulfate. By addition of such an inorganic salt, enzyme components involved especially in the xylan-degrading activity can be recovered in large amounts.

The concentration of the water-soluble inorganic salt added is preferably 0.05 to 5% by weight. When the concentration is less than 0.05% by weight, the recovery efficiency of cellulase may be low, while when the concentration is more than 5% by weight, deactivation of cellulase may be promoted and the process becomes economically disadvantageous. The washing temperature is not limited, and a temperature of 40 to 60° C. is preferred since cellulase can be efficiently recovered within such a temperature range.

The washing using the aqueous alkaline solution and the washing using the aqueous inorganic salt solution are independently carried out, and either of these may be carried out first. That is, the hydrolysis residue may be washed with the aqueous alkaline solution to recover an aqueous alkaline solution washing liquid as the first washing liquid, and the hydrolysis residue may then be washed with the aqueous inorganic salt solution to recover an aqueous inorganic salt solution washing liquid as the second washing liquid, or these washings may be carried out in the reverse order. For example, when the washing is carried out first with the aqueous alkaline solution and then with the aqueous inorganic salt solution, components involved in the cellobiose-degrading activity can be recovered in a larger amount. In contrast, when the washing is carried out first with the aqueous inorganic salt solution and then with the aqueous alkaline solution, components involved in the xylan-degrading activity can be recovered in a larger amount. The reason why the recovered enzyme components vary depending on the order of washing is that the alkali or inorganic salt remaining in the hydrolysis residue is carried over into the subsequent washing product. The washing method may be optimally determined depending on what enzyme component is to be recovered in a larger amount. It is helpful to reuse the recovered enzyme components in hydrolysis of a cellulose-containing biomass. Accordingly, the washing is preferably carried out first with the aqueous alkaline solution and then with the aqueous inorganic salt solution from the viewpoint of recovering larger amounts of the crystalline cellulose-degrading activity and the cellobiose-degrading activity, which are involved in degradation of cellulose, the constituting component occupying the largest part of the cellulose-containing biomass.

The amounts of the washing liquids for the washings of the hydrolysis residue are not limited and, in the first washing, the washing liquid is preferably added such that the solid concentration during the washing is from 1 to 20% by weight. In cases where the solid concentration is higher than 20% by weight, the washing is not efficient in view of the amount of enzyme recovered, while in cases where the solid concentration is lower than 1% by weight, the amount of the liquid is large, and the ultrafiltration membrane treatment in the Step (3) described below cannot be efficiently carried out.

In the second washing, the washing liquid is preferably added such that the solid concentration is 1 to 10% by weight. When the solid concentration is higher than 10% by weight, a large amount of the alkali or inorganic salt used in the first washing is brought over into the second washing and, therefore, enzyme components to be eluted in the second washing cannot be recovered in some cases. For example, when the washing is carried out first with the aqueous alkaline solution and then with the aqueous inorganic salt solution, the pH during the washing using the aqueous inorganic salt solution is influenced by the washing using the aqueous alkaline solution carried out in advance. Thus, enzyme components involved in the xylan-degrading activity, which should be recovered by the washing with the aqueous inorganic solution, may be deactivated. On the other hand, when the washing is carried out first with the aqueous inorganic salt solution and then with the aqueous alkaline solution, a high salt concentration in the washing using the aqueous alkaline solution may lead to a decrease in the recovery of the xylan-degrading activity. Conversely, when the solid concentration is less than 1% by weight, the amount of the liquid is large as in the first washing, and the ultrafiltration membrane treatment in the Step (3) described below cannot be efficiently carried out.

To avoid the above-described influence of the first washing liquid, the hydrolysis residue after the solid-liquid separation of the first washing product may be once immersed in water to wash off the alkali or inorganic salt remaining in the hydrolysis residue. In such a case, the amount of the washing liquid added for the second washing may be decreased to 20% by weight similarly to the first washing.

Alternatively, only when the washing is carried out first with the aqueous alkaline solution and then with the aqueous inorganic salt solution, an acid may be added during the washing with the aqueous inorganic salt solution to adjust the pH to a value at which cellulase is stable. The acid to be added is not limited, and examples of the acid include sulfuric acid, hydrochloric acid, citric acid, and acetic acid. As the pH during the washing using the aqueous inorganic salt solution decreases, the recovery of enzyme components involved in the xylan-degrading activity increases. On the other hand, as the pH increases, the recovery of enzyme components involved in the cellobiose-degrading activity increases. Thus, the pH during the washing using the aqueous inorganic salt solution may be set appropriately depending on what enzyme component is to be recovered in a larger amount.

Step (3)

The aqueous alkaline solution washing liquid and the aqueous inorganic salt solution washing liquid in the Step (2) are sequentially or simultaneously filtered through an ultrafiltration membrane to recover a sugar liquid as a permeate, and the filamentous fungus-derived cellulase as a non-permeate.

The molecular weight cutoff of the ultrafiltration membrane is not limited as long as the membrane allows permeation of glucose (molecular weight, 180) and xylose (molecular weight, 150), which are monosaccharides, but blocks the filamentous fungus-derived cellulase. More specifically, the molecular weight cutoff may be 500 to 50,000. From the viewpoint of separating impurities that show inhibitory actions against the enzymatic reaction from the enzyme, the molecular weight cutoff is more preferably 5,000 to 50,000, still more preferably 10,000 to 30,000.

Examples of the material of the ultrafiltration membrane include polyether sulfone (PES), polysulfone (PS), polyacrylonitrile (PAN), polyvinylidene fluoride (PVDF), regenerated cellulose, cellulose, cellulose ester, sulfonated polysulfone, sulfonated polyether sulfone, polyolefin, polyvinyl alcohol, polymethyl methacrylate, and polytetrafluoroethylene. Since regenerated cellulose, cellulose, and cellulose ester undergo degradation by cellulase, an ultrafiltration membrane using a synthetic polymer material such as PES or PVDF is preferably used.

Examples of the method of filtration through the ultrafiltration membrane include dead-end filtration and cross-flow filtration, and the method is preferably cross-flow filtration in view of suppression of membrane fouling. Examples of the form of the ultrafiltration membrane which may be used as appropriate include the flat membrane, spiral-wound membrane, tubular membrane and hollow fiber membrane. Specific examples of the ultrafiltration membrane include Type G-5, Type G-10, Type G-20, Type G-50, Type PW, and Type HWSUF, manufactured by DESAL; HFM-180, HFM-183, HFM-251, HFM-300, HFK-131, HFK-328, MPT-U20, MPS-U20P, and MPS-U205, manufactured by KOCH; SPE1, SPE3, SPE5, SPE10, SPE30, SPV5, SPV50, and SOW30, manufactured by Synder; products of Microza (registered trademark) UF series, manufactured by Asahi Kasei Corporation, having molecular weight cutoffs of 3000 to 10,000; and NTR7410 and NTR7450, manufactured by Nitto Denko Corporation.

Apparatus

The apparatus to carry out the method of producing a sugar liquid is described below, but the example of the apparatus is not limited to the following.

Figure 2:
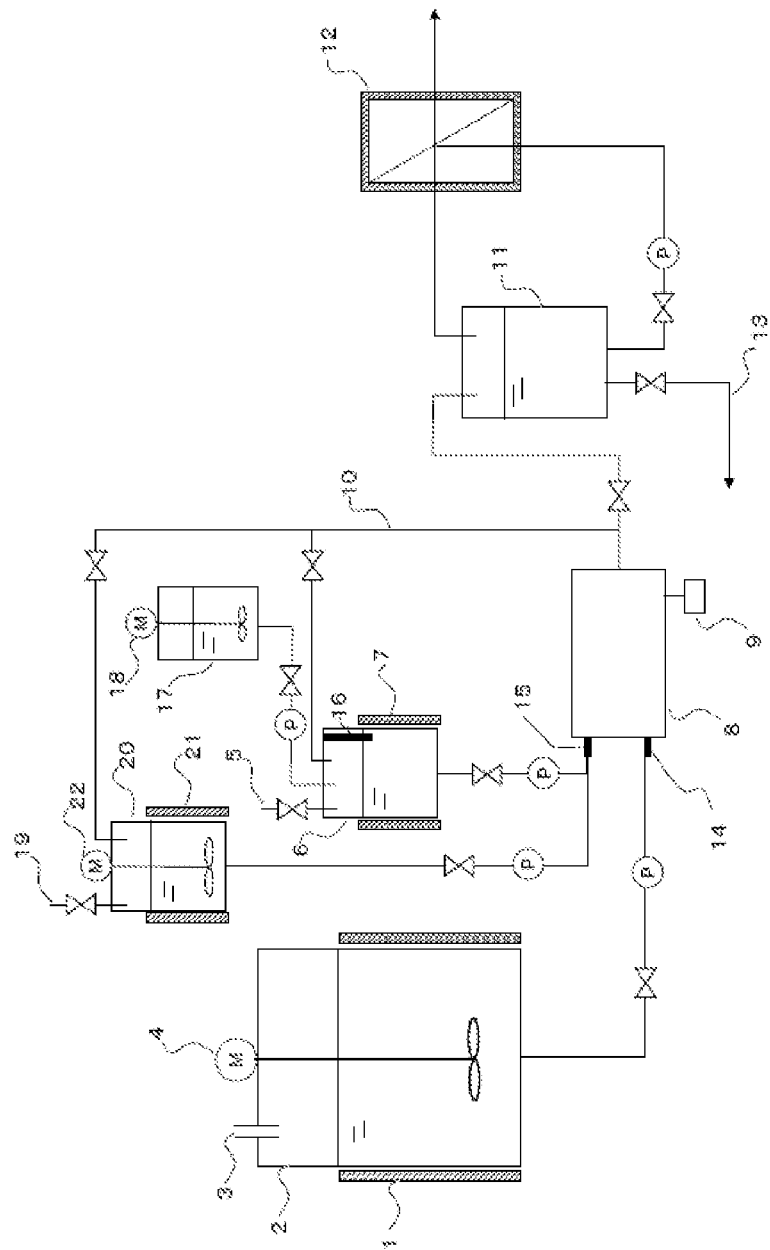
FIG. 2 is a schematic diagram showing an example of the apparatus to carry out our method of producing a sugar liquid.

An example of the apparatus include the apparatus shown in FIG. 2. The apparatus comprises a hydrolysis tank 2 and a press filtration device 8 as devices for carrying out Step (1). The hydrolysis tank 2 has an incubator (hydrolysis tank) 1, a cellulose-containing biomass inlet 3, and a stirrer (hydrolysis tank) 4. The solid-liquid separation device is composed of a press filtration device 8 and a compressor 9. The hydrolysate of the cellulose-containing biomass obtained in the hydrolysis tank 2 is fed from a hydrolysate inlet 14 into the press filtration device 8. In this process, compression is carried out with the compressor 9 to perform solid-liquid separation.

The apparatus comprises an aqueous alkaline solution supply tank 6, an aqueous inorganic salt solution supply tank 20, and a circulation line 10 as devices to carry out Step (2).

First, an example of the apparatus to carry out the washing using the aqueous alkaline solution is described. The aqueous alkaline solution to be used for the washing of the hydrolysis residue is supplied from the aqueous alkaline solution supply tank 6, and passes through a washing liquid port 15 into the press filtration device. Subsequently, the washing liquid can be circulated from the press filtration device 8 through the circulation line 10. The aqueous alkaline solution supply tank 6 has a water supply line (aqueous alkaline solution supply tank) 5, an incubator (aqueous alkaline solution supply tank) 7, a pH sensor 16 to measure the pH of the washing liquid, and a concentrated alkali supply tank 17 to adjust the pH of the washing liquid by adding a concentrated alkali dropwise depending on the pH of the washing liquid. The concentrated alkali supply tank 17 has a stirrer (concentrated alkali supply tank) 18.

An example of the apparatus to carry out the washing using the aqueous inorganic salt solution is now described. The aqueous inorganic salt solution is supplied from the aqueous inorganic salt solution supply tank 20. The aqueous inorganic salt solution supply tank 20 has an incubator (aqueous inorganic salt solution supply tank) 21 for adjusting the temperature of the washing liquid to a desired value, a water supply line (aqueous inorganic salt solution supply tank) 19, and a stirrer (aqueous inorganic salt solution supply tank) 22.

The apparatus comprises a filtrate recovery tank 11 and an ultrafiltration device 12 as devices to carry out Step (3). The washing liquid obtained in Step (2) is retained in the filtrate recovery tank 11 and then filtered through the ultrafiltration membrane device 12, for separation of cellulase from sugar. The cellulase recovered can be collected and/or reused through a cellulase collection line 13.

Since the apparatus shown in FIG. 2 has a simple apparatus constitution in which washing of the hydrolysis residue is carried out using the press filtration device 8 as a solid-liquid separation device, the cost for the apparatus can be suppressed, which is advantageous.

Other examples of the apparatus to carry out the method of producing a sugar liquid include an example in which the hydrolysis residue is transferred from a solid-liquid separation device into a washing tank, and the hydrolysis residue is then washed in the washing tank.

Use of Sugar Liquid

By using a sugar liquid obtained by our methods as a fermentation feedstock to grow microorganisms having capacity to produce chemical products, various chemicals can be produced. "Growing microorganisms using a sugar liquid as a fermentation feedstock" herein means that sugar components and/or amino sources contained in the sugar liquid are used as nutrients for microorganisms, to cause, and to allow continuation of, growth of the microorganisms. Specific examples of the chemical products include alcohols, organic acids, amino acids, and nucleic acids, which are substances mass-produced in the fermentation industry. Such chemical products are produced and accumulated inside and outside the living body as a result of metabolism using sugar components in the sugar liquid as carbon sources. Specific examples the chemical products that can be produced by microorganisms include alcohols such as ethanol, 1,3-propanediol, 1,4-butanediol, and glycerol; organic acids such as acetic acid, lactic acid, pyruvic acid, succinic acid, malic acid, itaconic acid, and citric acid; nucleosides such as inosine and guanosine; nucleotides such as inosinic acid and guanylic acid; and amine compounds such as cadaverine. Further, the sugar liquid can be applied to production of enzymes, antibiotics, recombinant proteins, and the like. The microorganisms used for production of such chemical products are not limited as long as the microorganisms are capable of efficiently producing the chemical products of interest, and examples of the microorganisms that may be used include microorganisms such as *E. coli*, yeasts, filamentous fungi, and Basidiomycetes.

EXAMPLES

Our methods are described below more concretely by way of Examples. However, this disclosure is not limited to these.

Reference Example 1: Preparation of Cellulose-Containing Biomass

1. Dilute Sulfuric Acid Treatment of Cellulose-Containing Biomass

A cellulose-containing biomass (corncob) was immersed in 1% aqueous sulfuric acid solution, and processed with an autoclave (manufactured by Nitto Koatsu Co., Ltd.) at 150° C. for 30 minutes. Thereafter, solid-liquid separation was carried out to achieve separation into an aqueous sulfuric acid solution (hereinafter referred to as dilute-sulfuric-acid-treated liquid) and sulfuric-acid-treated cellulose. Subsequently, the sulfuric-acid-treated cellulose was mixed with the dilute-sulfuric-acid-treated liquid by stirring such that the solid concentration became 10% by weight, and the pH of the resulting mixture was adjusted to about 5 using sodium hydroxide. The obtained dilute-sulfuric-acid-treated product was used in the following Examples.

2. Ammonia Treatment of Cellulose-Containing Biomass

A cellulose-containing biomass (*Erianthus*) was fed to a small reactor (manufactured by Taiatsu Techno Corporation, TVS-N2 30 mL), and cooled in liquid nitrogen. Ammonia gas was introduced into this reactor and the sample was completely immersed in liquid ammonia. The lid of the reactor was closed, and the reactor left to stand at room temperature for about 15 minutes. Subsequently, the reactor was processed in an oil bath at 150° C. for 1 hour. Thereafter, the reactor was removed from the oil bath, and the ammonia gas was immediately leaked in a fume hood, followed by vacuuming the inside of the reactor to 10 Pa with a vacuum pump, thereby drying the content. The obtained ammonia-treated product was used in the Examples below.

Reference Example 2: Measurement of Sugar Concentration

For measurement of the sugar concentration, Glucose CII-Test Wako (manufactured by Wako Pure Chemical Industries, Ltd.) was used, and, for measurement of the xylose concentration, D-XYLOSE ASSAY KIT (manufactured by Megazyme) was used.

Reference Example 3: Preparation of *Trichoderma*-Derived Cellulase

*Trichoderma*-derived cellulase was prepared by the following method.
Preculture
The mixture of 5% (w/v) corn steep liquor, 2% (w/v) glucose, 0.37% (w/v) ammonium tartrate, 0.14% (w/v) ammonium sulfate, 0.14% (w/v) potassium dihydrogen phosphate, 0.03% (w/v) calcium chloride dihydrate, 0.03% (w/v) magnesium sulfate heptahydrate, 0.02% (w/v) zinc chloride, 0.01% (w/v) iron (III) chloride hexahydrate, 0.004% (w/v) copper (II) sulfate pentahydrate, 0.0008% (w/v) manganese chloride tetrahydrate, 0.0006% (w/v) boric acid, and 0.026% (w/v) hexaammonium heptamolybdate tetrahydrate dissolved in distilled water was prepared and 100 mL of this mixture placed in a baffled 500-mL Erlenmeyer flask, followed by sterilization by autoclaving at 121° C. for 15 minutes. After allowing the mixture to cool, PE-M and Tween 80, each of which was sterilized by autoclaving at 121° C. for 15 minutes separately from the mixture, were added to the mixture at 0.01% (w/v) each. To this preculture medium, *Trichoderma reesei* PC3-7 was inoculated at 1×10$^5$ cells/mL, and the cells cultured at 28° C. for 72 hours with shaking at 180 rpm, to provide a preculture liquid (shaker: BIO-SHAKER BR-40LF, manufactured by TAITEC CORPORATION).

Main Culture

The mixture of 5% (w/v) corn steep liquor, 2% (w/v) glucose, 10% (w/v) cellulose (AVICEL), 0.37% ammonium tartrate (w/v), 0.14% (w/v) ammonium sulfate, 0.2% (w/v) potassium dihydrogen phosphate, 0.03% (w/v) calcium chloride dihydrate, 0.03% (w/v) magnesium sulfate heptahydrate, 0.02% (w/v) zinc chloride, 0.01% (w/v) iron (III) chloride hexahydrate, 0.004% (w/v) copper (II) sulfate pentahydrate, 0.0008% (w/v) manganese chloride tetrahydrate, 0.006% (w/v) boric acid, and 0.0026% (w/v) hexaammonium heptamolybdate tetrahydrate dissolved in distilled water was prepared, and 2.5 L of this mixture was placed in a 5-L jar fermenter (manufactured by ABLE, DPC-2A), followed by sterilization by autoclaving at 121° C. for 15 minutes. After allowing the mixture to cool, PE-M and Tween 80, each of which was sterilized by autoclaving at 121° C. for 15 minutes separately from the mixture, were added to the mixture at 0.01% (w/v) each. To the resulting mixture, 250 mL of the preculture liquid obtained by the above method was inoculated. The cells were then cultured at 28° C. for 87 hours at 300 rpm at an aeration rate of 1 vvm. The obtained culture liquid was used as it is as a crude enzyme liquid in the Examples below.

Reference Example 4: Method of Measuring Cellulase Activity

The cellulase activity was measured and evaluated by the following procedures in terms of 3 types of degradation activities: 1) crystalline cellulose-degrading activity; 2) cellobiose-degrading activity; and 3) xylan-degrading activity.

1) Crystalline Cellulose-Degrading Activity

In 50 mM sodium acetate buffer (pH 5.2), crystalline cellulose (Cellulose microcrystalline, manufactured by Merck) was suspended at 1% by weight to provide a substrate solution. To 500 µL of the substrate solution, 5 µL of the enzyme liquid was added, and the reaction allowed to proceed while the mixture was mixed by rotation at 50° C. The reaction was carried out for 24 hours. Thereafter, the tube was centrifuged and the glucose concentration in the supernatant component measured. The measurement of the glucose concentration was carried out by the method described in Reference Example 2. The amount of enzyme that produces 1 µmol of glucose per minute in the above reaction system was defined as 1 U, and the activity value (U/mL) calculated according to the following equation:

$$\text{Crystalline cellulose-degrading activity (U/mL)} = \text{glucose concentration (g/L)} \times 1000 \times 505 \,(\mu L)/(180.16 \times \text{reaction time (minutes)} \times 5 \,(\mu L)).$$

2) Cellobiose-Degrading Activity

In 50 mM sodium acetate buffer (pH 5.2), D(+)-cellobiose (manufactured by Wako Pure Chemical Industries, Ltd.) was dissolved at 15 mM to provide a substrate solution. To 500 µL of the substrate solution, 5 µL of the enzyme liquid was added, and the reaction allowed to proceed while the mixture was mixed by rotation at 50° C. The reaction was basically carried out for 0.5 hour, but the reaction time was changed as appropriate depending on the level of the activity. Thereafter, the tube was centrifuged, and the glucose concentration in the supernatant component measured. The measurement of the glucose concentration was carried out by the method described in Reference Example 2. The amount of enzyme that produces 1 µmol of glucose per minute in the above reaction system was defined as 1 U, and the activity value (U/mL) calculated according to the following equation:

Cellobiose-degrading activity (U/mL)=glucose concentration (g/L)×1000×505 (μL)/(180.16×reaction time (minutes)×5 (μL)).

3) Xylan-Degrading Activity

In 50 mM sodium acetate buffer (pH 5.2), xylan (Xylan from Birch wood, manufactured by Fluka) was suspended at 1% by weight to provide a substrate solution. To a 500-μL aliquot of the substrate solution, 5 μL of the enzyme liquid was added, and the reaction allowed to proceed while the mixture was mixed by rotation at 50° C. The reaction was basically carried out for 4 hours, but the reaction time was changed as appropriate depending on the level of the activity. Thereafter, the tube was centrifuged, and the xylose concentration in the supernatant component measured. The measurement of the xylose concentration was carried out by the method described in Reference Example 2. The amount of enzyme that produces 1 μmol of xylose per minute in the above reaction system was defined as 1 U, and the activity value (U/mL) calculated according to the following equation:

Xylan-degrading activity (U/mL)=xylose concentration (g/L)×1000×505 (μL)/(150.13×reaction time (minutes)×5 (μL)).

Comparative Example 1: Recovery of Enzyme by One Time of Washing of Residue

As a Comparative Example, the hydrolysis residue was washed using only one of the aqueous alkaline solution and the aqueous inorganic salt solution, and the enzyme recovery was investigated as follows.

Step 1: Hydrolysis of Cellulose-Containing Biomass

In each of four 50-mL centrifuge tubes, 1 g of a dilute-sulfuric-acid-treated product or ammonia-treated product of the cellulose-containing biomass was placed, and ultrapure water added thereto such that the final concentration of the pretreated biomass was 10% (w/w). Using dilute sulfuric acid or sodium hydroxide dilution, the pH of the composition was adjusted to a value of 4.0 to 6.0. To the composition whose pH was adjusted, 30 mg of Trichoderma-derived cellulase was added, and the resulting mixture mixed by rotation using a hybridization rotator (manufactured by Nissin Rika, SN-06BN) at 50° C. for 24 hours. The obtained hydrolysate was centrifuged (8000 G, 10 minutes) to perform solid-liquid separation, to obtain 8 g of a sugar liquid and 2 g of a hydrolysis residue.

Step 2: Washing of Hydrolysis Residue with Aqueous Alkaline Solution

To each of 2 samples of the hydrolysis residue obtained in Step 1, ultrapure water was added to a total weight of 10 g, and the pH of one of these adjusted to 9 using a sodium hydroxide dilution. For comparison, no alkali was added to the other sample (no pH adjustment). These washing samples were mixed by rotation using a hybridization rotator (manufactured by Nissin Rika, SN-06BN) at 25° C. for 1 hour. Each washing product was then centrifuged (8000 G, 10 minutes) to perform solid-liquid separation, to obtain 8 g of a washing liquid and 2 g of a hydrolysis residue.

Step 2': Washing of Hydrolysis Residue with Aqueous Inorganic Salt Solution

To each of 2 samples of the hydrolysis residue obtained in Step 1, 2% by weight aqueous sodium chloride solution was added to a total weight of 10 g, and the pH of one of these was not adjusted. For comparison, caustic soda dilution was added to the other sample to adjust the pH to 9. These washing samples were mixed by rotation using a hybridization rotator (manufactured by Nissin Rika, SN-06BN) for 1 hour. The sample at pH 9 was washed at 25° C., and the sample whose pH was not adjusted was washed at 50° C. Each washing product was then centrifuged (8000 G, 10 minutes) to perform solid-liquid separation, to obtain 8 g of a washing liquid and 2 g of a hydrolysis residue.

Step 3: Ultrafiltration

The sugar solution obtained in Step 1 and the washing liquid obtained in Step 2 or Step 2' were combined and filtered through an ultrafiltration membrane having a molecular weight cutoff of 10,000 (manufactured by Sartorius stedim biotech; VIVASPIN 20; material: PES), followed by performing centrifugation at 8000 G such that the amount of the liquid in the feed side became not more than 1 mL. The non-permeate was diluted 10-fold with ultrapure water, and centrifuged again at 8000 G, to provide the non-permeate as a recovered enzyme liquid. The obtained recovered enzyme liquid was subjected to measurement of the activities according to Reference Example 4 (Table 1).

TABLE 1

| | | | Activity value (U/mL) | | |
|---|---|---|---|---|---|
| | Washing liquid | pH | Crystalline cellulose-degrading activity | Cellobiose-degrading activity | Xylan-degrading activity |
| Dilute-sulfuric-acid treated product | Ultrapure water (25° C.) | Not adjusted (about 5) | $1.5 \times 10^{-5}$ | 0.08 | 0.03 |
| | Ultrapure water (25° C.) | 9 | $2.1 \times 10^{-5}$ | 0.11 | 0.13 |
| | Sodium chloride (50° C.) | Not adjusted (about 5) | $1.4 \times 10^{-5}$ | 0.07 | 0.04 |
| | Sodium chloride (25° C.) | 9 | $2.9 \times 10^{-5}$ | 0.30 | 0.04 |
| Ammonia-treated product | Ultrapure water (25° C.) | Not adjusted (about 5) | 1.0 | 4.0 | 10 |
| | Ultrapure water (25° C.) | 9 | 1.2 | 5.8 | 15 |
| | Sodium chloride (50° C.) | Not adjusted (about 5) | 1.2 | 5.4 | 14 |
| | Sodium chloride (25° C.) | 9 | 1.2 | 5.2 | 13 |

Comparative Example 2: Recovery of Enzyme by Two Times of Washing of Residue Using Same Type of Washing Liquid To the hydrolysis residues obtained by the solid-liquid separation in Step 2 and Step 2' of Comparative Example 1, the same washing liquid as in the first washing was added, and the second washing carried out. All of the sugar solution, the first washing liquid, and the second washing liquid were combined, and a recovered enzyme liquid obtained by the same method as in Step 3 of Comparative Example 1. The recovered enzyme liquid was subjected to measurement of the activities according to Reference Example 4 (Table 2).

inorganic salt solution (2% by weight sodium chloride, 50° C.); or the washings of the hydrolysis residue were carried out in the reverse order. A recovered enzyme was obtained from the sugar solution and the washing liquid by the same method as in Step 3 of Comparative Example 1, and subjected to measurement of the activities according to Reference Example 4. The results are summarized as relative activities in Table 3 and Table 4. Both when the dilute-sulfuric-acid-treated product was used and when the ammonia-treated product was used, the two times of washing using the different washing liquids resulted in recovery of more enzyme components than the only one time of washing or the two times of washing using the same type of

TABLE 2

| | | | Activity value (U/mL) | | |
|---|---|---|---|---|---|
| | Washing liquid | pH | Crystalline cellulose- degrading activity | Cellobiose- degrading activity | Xylan- degrading activity |
| Dilute-sulfuric-acid- treated product | Ultrapure water (25° C.) | 9 | $2.7 \times 10^{-5}$ | 0.16 | 0.15 |
| | Sodium chloride (50° C.) | Not adjusted (about 5) | $1.8 \times 10^{-5}$ | 0.10 | 0.05 |
| Ammonia-treated product | Ultrapure water (25° C.) | 9 | 1.4 | 6.4 | 23 |
| | Sodium chloride (50° C.) | Not adjusted (about 5) | 1.1 | 4.8 | 23 |

Example 1: Effect of Combination of Different Washing Liquids

Both Step 2 and Step 2' of Comparative Example 1 were carried out, and the enzyme recovery investigated as follows. More specifically, the first washing was carried out with an aqueous sodium hydroxide solution (pH 9, 25° C.), and the second washing then carried out with an aqueous washing liquid. In particular, a remarkable effect could be obtained when the dilute-sulfuric-acid-treated product was used. The washing using the aqueous sodium hydroxide solution and the aqueous inorganic salt solution in this order tended to result in recovery of a larger amount of the cellobiose-degrading activity, and the washing using the aqueous inorganic salt solution and the aqueous sodium hydroxide solution in this order tended to result in recovery of a larger amount of the xylan-degrading activity.

TABLE 3

| | Dilute-sulfuric-acid-treated product | | Relative activity | | |
|---|---|---|---|---|---|
| | | | Crystalline cellulose- degrading activity | Cellobiose- degrading activity | Xylan- degrading activity |
| | First washing | Second washing | | | |
| Comparative Example 1 | No pH adjustment | — | 1.0 | 1.0 | 1.0 |
| | Sodium hydroxide (pH 9) | — | 1.4 | 1.5 | 3.2 |
| | Sodium chloride | — | 0.9 | 0.9 | 1.4 |
| | Sodium chloride (pH 9) | — | 1.9 | 3.8 | 1.3 |
| Comparative Example 2 | Sodium hydroxide (pH 9) | Sodium hydroxide (pH 9) | 1.8 | 2.0 | 3.8 |
| | Sodium chloride | Sodium chloride | 1.3 | 1.2 | 1.7 |
| Example 1 | Sodium hydroxide (pH 9) | Sodium chloride | 3.1 | 5.4 | 5.0 |
| | Sodium chloride | Sodium hydroxide (pH 9) | 3.2 | 2.1 | 7.1 |

TABLE 4

| | Ammonia-treated product | | Relative activity | | |
|---|---|---|---|---|---|
| | First washing | Second washing | Crystalline cellulose-degrading activity | Cellobiose-degrading activity | Xylan-degrading activity |
| Comparative Example 1 | No pH adjustment | — | 1.0 | 1.0 | 1.0 |
| | Sodium hydroxide (pH 9) | — | 1.2 | 1.4 | 1.4 |
| | Sodium chloride | — | 1.0 | 1.3 | 1.3 |
| | Sodium chloride (pH 9) | — | 1.2 | 1.3 | 1.3 |
| Comparative Example 2 | Sodium hydroxide (pH 9) | Sodium hydroxide (pH 9) | 1.4 | 1.6 | 1.5 |
| | Sodium chloride | Sodium chloride | 1.1 | 1.2 | 1.5 |
| Example 1 | Sodium hydroxide (pH 9) | Sodium chloride | 1.8 | 2.3 | 2.5 |
| | Sodium chloride | Sodium hydroxide (pH 9) | 1.3 | 2.2 | 2.0 |

Example 2: Association Between Type of Alkali Used for First Washing and Recovery of Enzyme The first washing was carried out in the same manner as in Example 1 (dilute-sulfuric-acid-treated product) at 25° C. for 1 hour except that sodium hydroxide, potassium hydroxide, ammonia, sodium carbonate, or trisodium phosphate was used as the alkali for the first washing liquid after adjustment of the pH to 9. Subsequently, 2% by weight aqueous sodium chloride solution was added as the second washing liquid, and washing carried out at 50° C. for 1 hour. Thereafter, a recovered enzyme liquid obtained by the same method as in Step 3 of Comparative Example 1 was used for measurement of the activities according to Reference Example 4. Using, as a standard (activity=1.0), the activity of enzyme recovered under conditions where only the first washing was carried out without adjustment of the pH, the relative activity calculated. The results are shown in Table 5. Compared to when no alkali was used for the first washing, more enzyme components could be recovered when sodium hydroxide, potassium hydroxide, ammonia, sodium carbonate, or trisodium phosphate was used as the alkali for the first washing liquid. In particular, when ammonia was used, the enzyme component involved in the crystalline cellulose-degrading activity could be recovered in the largest amount.

TABLE 5

| Dilute-sulfuric-acid-treated product | | Relative activity | | |
|---|---|---|---|---|
| First washing | Second washing | Crystalline cellulose-degrading activity | Cellobiose-degrading activity | Xylan-degrading activity |
| No pH adjustment (about pH 5) (Comparative Example 1) | — | 1.0 | 1.0 | 1.0 |
| Sodium hydroxide (pH 9) (Example 1) | Sodium chloride | 3.1 | 5.4 | 5.0 |
| Potassium hydroxide (pH 9) | | 3.0 | 5.5 | 5.1 |
| Ammonia (pH 9) | | 3.5 | 5.4 | 5.3 |

TABLE 5-continued

| Dilute-sulfuric-acid-treated product | | Relative activity | | |
|---|---|---|---|---|
| First washing | Second washing | Crystalline cellulose-degrading activity | Cellobiose-degrading activity | Xylan-degrading activity |
| Sodium carbonate (pH 9) | | 3.2 | 5.3 | 5.1 |
| Trisodium phosphate (pH 9) | | 2.9 | 5.1 | 4.8 |

Example 3: Influence of pH During Washing (First Washing Using Sodium Hydroxide)

The first washing was carried out in the same manner as in Example 1 (ammonia-treated product) at 25° C. for 1 hour except that sodium hydroxide was used as the alkali for the first washing liquid to adjust the pH to different values within the range of 7.5 to 12.0. Subsequently, 2% by weight aqueous sodium chloride solution was added as the second washing liquid, and washing carried out at 50° C. for 1 hour. Thereafter, a recovered enzyme liquid obtained by the same method as in Step 3 of Comparative Example 1 was used for measurement of the activities according to Reference Example 4. Using, as a standard (activity=1.0), the activity of enzyme recovered after carrying out the first washing without adjustment of the pH and then carrying out the second washing in the same manner, the relative activity was calculated. The results are shown in Table 6.

TABLE 6

| | Relative activity | | |
|---|---|---|---|
| Condition for first washing (Sodium hydroxide) | Crystalline cellulose-degrading activity | Cellobiose-degrading activity | Xylan-degrading activity |
| No pH adjustment (about pH 5) | 1.0 | 1.0 | 1.0 |
| pH 7.5 | 1.0 | 1.1 | 2.1 |
| pH 8.0 | 1.1 | 1.2 | 2.0 |
| pH 8.5 | 1.1 | 1.5 | 1.8 |

TABLE 6-continued

| Condition for first washing (Sodium hydroxide) | Relative activity | | |
|---|---|---|---|
| | Crystalline cellulose-degrading activity | Cellobiose-degrading activity | Xylan-degrading activity |
| pH 9.0 (Example 1) | 1.2 | 1.8 | 1.7 |
| pH 9.5 | 1.3 | 1.9 | 1.6 |
| pH 10.0 | 1.1 | 1.9 | 1.4 |
| pH 11.0 | 0.9 | 1.7 | 0.8 |
| pH 12.0 | 0.5 | 0.7 | 0.2 |

Larger amounts of enzyme could be recovered within the pH range of 7.5 to 10.0 compared to when the pH was not adjusted. When the pH was low in the first washing, a larger amount of the xylan-degrading activity could be recovered and, when the pH was high, larger amounts of the crystalline cellulose-degrading activity and the cellobiose-degrading activity could be recovered.

Example 4: Influence of pH During Washing (First Washing Using Ammonia)

The first washing was carried out in the same manner as in Example 3 except that dilute-sulfuric-acid-treated product was used as the cellulose-containing biomass, and ammonia was used as the alkali for the first washing liquid. Thereafter, the second washing was carried out by the same method as in Example 3, to obtain a recovered enzyme liquid. The obtained recovered enzyme liquid was subjected to measurement of the activities according to Reference Example 4. Using, as a standard (activity=1.0), the activity of enzyme recovered after carrying out the first washing without adjustment of the pH and then carrying out the second washing in the same manner, the relative activity was calculated. The results are shown in Table 7. Similarly to when sodium hydroxide was used, use of ammonia as the alkali for the first washing liquid resulted in recovery of larger amounts of enzyme within the pH range of 7.5 to 10.0 compared to when the pH was not adjusted.

TABLE 7

| Condition for first washing (Ammonia) | Relative activity | | |
|---|---|---|---|
| | Crystalline cellulose-degrading activity | Cellobiose-degrading activity | Xylan-degrading activity |
| No pH adjustment (about pH 5) | 1.0 | 1.0 | 1.0 |
| pH 7.5 | 1.1 | 1.5 | 4.3 |
| pH 8.0 | 1.3 | 2.6 | 4.3 |
| pH 8.5 | 2.0 | 3.7 | 4.4 |
| pH 9.0 (Example 2) | 2.4 | 4.2 | 3.7 |
| pH 9.5 | 2.6 | 4.6 | 3.4 |
| pH 10.0 | 2.3 | 4.7 | 2.8 |
| pH 11.0 | 0.8 | 4.2 | 0.9 |
| pH 12.0 | 0.4 | 0.9 | 0.1 |

Example 5: Association Between pH and Temperature During Washing

The first washing was carried out in the same manner as in Example 3 or Example 4 except that the washing was carried out at different temperatures within the range of 25 to 50° C. Subsequently, 2% by weight aqueous sodium chloride solution was added as the second washing liquid, and washing carried out at 50° C. for 1 hour. Thereafter, a recovered enzyme liquid obtained by the same method as in Step 3 of Comparative Example 1 was used for measurement of the activities according to Reference Example 4. The first washing was carried out at 25° C. at each pH to provide a standard (activity=1.0). The results obtained using sodium hydroxide as the alkali for the first washing are shown in Table 8, and the results obtained using ammonia are shown in Table 9 as relative activities.

TABLE 8

| Conditions for first washing (Sodium hydroxide) | | Relative activity | | |
|---|---|---|---|---|
| | | Crystalline cellulose-degrading activity | Cellobiose-degrading activity | Xylan-degrading activity |
| pH 7.5 | 25° C. (Example 3) | 1.0 | 1.0 | 1.0 |
| | 40° C. | 1.3 | 1.2 | 1.5 |
| | 50° C. | 1.1 | 1.1 | 1.2 |
| pH 9.0 | 25° C. (Example 1) | 1.0 | 1.0 | 1.0 |
| | 40° C. | 1.1 | 1.1 | 1.0 |
| | 50° C. | 1.0 | 0.9 | 0.8 |
| pH 10.0 | 25° C. (Example 3) | 1.0 | 1.0 | 1.0 |
| | 40° C. | 1.0 | 1.0 | 0.9 |
| | 50° C. | 0.8 | 0.9 | 0.7 |

TABLE 9

| Conditions for first washing (Ammonia) | | Relative activity | | |
|---|---|---|---|---|
| | | Crystalline cellulose-degrading activity | Cellobiose-degrading activity | Xylan-degrading activity |
| pH 7.5 | 25° C. (Example 4) | 1.0 | 1.0 | 1.0 |
| | 40° C. | 1.5 | 1.8 | 2.1 |
| | 50° C. | 1.4 | 1.4 | 1.7 |
| pH 9.0 | 25° C. (Example 2) | 1.0 | 1.0 | 1.0 |
| | 40° C. | 1.2 | 1.3 | 1.0 |
| | 50° C. | 0.6 | 0.7 | 0.4 |
| pH 10.0 | 25° C. (Example 4) | 1.0 | 1.0 | 1.0 |
| | 40° C. | 1.0 | 1.1 | 0.9 |
| | 50° C. | 0.5 | 0.8 | 0.2 |

Both when sodium hydroxide was used and when ammonia was used as the alkali for the first washing liquid, deactivation of cellulase was found when the temperature during the washing with the aqueous alkaline solution was higher than 40° C., and the highest enzyme recovery within the pH range of 7.5 to 10.0 was achieved at a temperature of not more than 40° C. in all cases.

Example 6: Association Between Type of Inorganic Salt and Recovery of Enzyme

By the same method as in Example 1, washing was carried out at pH 9 at 25° C. for 1 hour using sodium hydroxide as the alkali for the first washing, and an aqueous alkaline solution washing liquid collected as the first washing liquid. Thereafter, the second washing was carried out using an aqueous inorganic salt solution, and an aqueous inorganic salt solution washing liquid was collected as the second washing liquid. As the inorganic salt, sodium chloride, potassium chloride, magnesium chloride, or ammonium sulfate was used. Similarly to Example 1, the concentration of the aqueous inorganic salt solution was 2% by weight, and the washing carried out at 50° C. for 1 hour. All of the sugar solution, the first washing liquid, and the second washing liquid were combined, and a recovered enzyme liquid was obtained by the same method as in Step 3 of Comparative Example 1. The recovered enzyme liquid was subjected to measurement of the activities according to Reference Example 4. For each condition, the result obtained by carrying out the second washing using the aqueous sodium chloride solution was used as a standard (activity=1.0). The results are shown in Table 10.

TABLE 10

| Condition for second washing | Relative activity | | |
|---|---|---|---|
| | Crystalline cellulose-degrading activity | Cellobiose-degrading activity | Xylan-degrading activity |
| Sodium chloride (Example 1) | 1.0 | 1.0 | 1.0 |
| Potassium chloride | 1.0 | 1.1 | 0.9 |
| Magnesium chloride | 1.2 | 0.9 | 1.1 |
| Ammonium sulfate | 1.0 | 1.1 | 1.0 |

The amounts of enzyme recovered when the second washing was carried out using potassium chloride, magnesium chloride, or ammonium sulfate were equivalent to or larger than when sodium chloride was used.

INDUSTRIAL APPLICABILITY

The sugar liquid obtained by our methods can be used as a sugar material for various fermentation products.

The invention claimed is:

1. A method of producing a sugar liquid from a cellulose-containing biomass, comprising:
   (1) hydrolyzing a cellulose-containing biomass using a filamentous fungus-derived cellulase and carrying out solid-liquid separation into a sugar liquid and a hydrolysis residue;
   (2) washing the hydrolysis residue in (1) with an aqueous alkaline solution and recovering an aqueous alkaline solution washing liquid as a first washing liquid to recover the filamentous fungus-derived cellulase adsorbed to the hydrolysis residue;
   (3) further washing the washed hydrolysis residue in (2) with an aqueous inorganic salt solution and recovering an aqueous inorganic salt solution washing liquid as a second washing liquid to recover the filamentous fungus-derived cellulase adsorbed to the hydrolysis residue; and
   (4) filtering the washing liquid in (2) and (3) through an ultrafiltration membrane to recover a sugar liquid as a permeate and the filamentous fungus-derived cellulase as a non-permeate,
   wherein the pH of the aqueous alkaline solution in (2) is 7.5 to 10.0, and
   the aqueous inorganic salt solution in (3) comprises one or more inorganic salt(s) selected from the group consisting of sodium chloride, potassium chloride, magnesium chloride and ammonium sulfate as major inorganic salt component(s).

2. The method according to claim 1, wherein the temperature of the aqueous alkaline solution in (2) is not more than 40° C.

3. The method according to claim 2, wherein the alkali in (2) is ammonia, sodium hydroxide, potassium hydroxide, sodium carbonate, and/or trisodium phosphate.

4. The method according to claim 1, wherein the alkali in (2) is ammonia, sodium hydroxide, potassium hydroxide, sodium carbonate, and/or trisodium phosphate.

5. The method according to claim 1, wherein the filamentous fungus-derived cellulase in (1) is derived from a microorganism(s) belonging to the genus *Trichoderma*.

6. The method according to claim 1, wherein, in (1), a cellulose-containing biomass treated with dilute sulfuric acid is hydrolyzed.

7. The method according to claim 1, wherein the hydrolysis residue is obtained by press filtration in (1).

8. The method according to claim 1, further comprising filtering the sugar liquid obtained in (4) through a nanofiltration membrane and/or reverse osmosis membrane to recover a concentrated sugar liquid as a non-permeate.

* * * * *